(12) United States Patent
Harn et al.

(10) Patent No.: US 9,018,251 B2
(45) Date of Patent: Apr. 28, 2015

(54) METHOD FOR TREATING BRAIN CANCER OR REDUCING TEMOZOLOMIDE-RESISTANCE OF BRAIN CANCER CELLS

(75) Inventors: Horng-Jyh Harn, Taichung (TW); Shinn-Zong Lin, Taichung (TW); Tzyy-Wen Chiou, Taichung (TW); Po-Cheng Lin, Taichung (TW)

(73) Assignee: China Medical University, Taichung (TW)

( * ) Notice: Subject to any disclaimer, the term of this patent is extended or adjusted under 35 U.S.C. 154(b) by 225 days.

(21) Appl. No.: 13/109,619

(22) Filed: May 17, 2011

(65) Prior Publication Data

US 2012/0178803 A1 Jul. 12, 2012

(30) Foreign Application Priority Data

Jan. 7, 2011 (TW) .............................. 100100673 A

(51) Int. Cl.
*A61K 31/343* (2006.01)
*A61K 31/4188* (2006.01)

(52) U.S. Cl.
CPC ........... *A61K 31/343* (2013.01); *A61K 31/4188* (2013.01)

(58) Field of Classification Search
CPC ... A61K 31/343; A61K 31/434; C07D 307/88
See application file for complete search history.

(56) References Cited

U.S. PATENT DOCUMENTS

| | | | |
|---|---|---|---|
| 7,455,861 | B2 | 11/2008 | Luo et al. |
| 2007/0112053 | A1 | 5/2007 | Pickett et al. |
| 2007/0237714 | A1* | 10/2007 | Alvarez ...................... 424/1.69 |
| 2009/0220551 | A1 | 9/2009 | Sampson et al. |
| 2010/0047167 | A1 | 2/2010 | Bigner et al. |
| 2010/0087499 | A1 | 4/2010 | Wang et al. |
| 2011/0165201 | A1 | 7/2011 | Chiou et al. |
| 2012/0045524 | A1 | 2/2012 | Wernet et al. |

FOREIGN PATENT DOCUMENTS

| | | |
|---|---|---|
| CA | 2 615 200 | 7/2009 |
| CA | 2615200 | 7/2009 |
| CN | 1943606 A | 4/2007 |
| EP | 1645280 | 4/2006 |
| EP | 2343051 | 7/2011 |
| JP | 2006-117663 | 5/2006 |
| JP | 2008-540429 | 11/2008 |
| JP | 2009-508868 | 3/2009 |
| JP | 2009-518287 | 5/2009 |
| JP | 2009-523801 | 6/2009 |
| JP | 2010-516771 | 5/2010 |
| JP | 2011-173866 | 9/2011 |
| TW | 1 298 259 | 7/2008 |
| WO | 2010/012777 A1 | 2/2010 |

OTHER PUBLICATIONS

Tsai et al 'The natural compound n-butylidenephthalide derived from *Angelica sinesis* inhibits malignant brain tumor growth in vitro and in vivo' Journal of Neurochemistry, vol. 99, p. 1251-1262, 2006.*
Nguyen et al 'Chiral Drugs: An Overview' International Journal of Biomedical Science, 2(2), p. 85-100, 2006.*
Extended European Search Report dated Jan. 2, 2012 of International Application No. 11176117.7.
Yu, Y.L., et al., "Extended $O^6$-Methylguanine Methyltransferase Promoter Hypermethylation Following n-Butylidenephthalide Combined with 1,3-Bis(2-chloroethyl)-1-nitrosourea (BCNU) on Inhibition of Human Hepatocellular Carcinoma Cell Growth", Journal of Agricultural and Food Chemistry, 2010, vol. 58, pp. 1630-1638.
Ranson, M. et. al., Randomized Trial of the Combination of Lomeguatrib and Temozolomide Compared With Temozolomide Alone in Chemotherapy Naïve Patients With Metastatic Cutaneous Melanoma, Journal of Clinical Oncology, 2007, vol. 25:2540-5.
Chou, T. et al., Quantitative analysis of dose-effect relationships: the combined effects of multiple drugs or enzyme inhibitors. Adv. Enzyme Regul., 22:27-55, 1984.
Pauwels, R. et al., Rapid and automated tetrazolium-based colorimetric assay for the detection of anti-HIV compounds, J. Virol. Methods, 1988, 20, 309-321.
Taiwan Office Action of Application No. 100100673 mailed Oct. 12, 2012.
Kitange, G. J. et al., "Induction of MGMT expression is associated with temozolomide resistance in glioblastoma xenografts", Jun. 2009, pp. 281-282, Society for Neuro-Oncology.
Tsai, N.M., et al., "The natural compound n-butylidenephthalide derived from *Angelica sinensis* inhibits malignant brain tumor growth in vitro and in vivo3", 2006, pp. 1251-1262, vol. 99, Journal of Neurochemistry.

* cited by examiner

*Primary Examiner* — Wu-Cheng Winston Shen
*Assistant Examiner* — Christopher R Stone
(74) *Attorney, Agent, or Firm* — Ping Wang; Andrews Kurth LLP

(57) ABSTRACT

Provided is a method for treating brain cancer or reducing temozolomide-resistance of brain cancer cells in a subject, comprising administrating to the subject an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof:

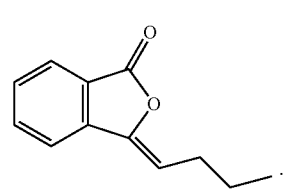

(I)

7 Claims, 8 Drawing Sheets

METHOD FOR TREATING BRAIN CANCER OR REDUCING TEMOZOLOMIDE-RESISTANCE OF BRAIN CANCER CELLS

CROSS-REFERENCES TO RELATED APPLICATIONS

This application claims the benefit of Taiwan Patent Application No. 100100673, filed on Jan. 7, 2011 in the Taiwan Intellectual Property Office, the disclosure of which is incorporated herein in its entirety by reference.

FIELD

The present invention relates to a method for reducing temozolomide-resistance of brain cancer cells, and particularly, relates to a method for reducing temozolomide-resistance of human malignant glioma.

BACKGROUND

Malignant brain tumor accounts for about 2% of malignant neoplasm cases. In spite of the low occurrence rate of malignant brain tumor, it is difficult to prevent because there is no specific carcinogenic factor for this disease. Brain tumors comprise primary brain tumors growing from the brain or other related cell and metastatic brain tumors from cancerous cells of other parts of the body. The outbreak of brain cancer is generally slow and takes a few weeks to several years. Symptoms of brain cancer include nausea, headache or dysfunction of consciousness caused by the increase of brain pressure, seizure, hormonal abnormalities, and partial cerebral dysfunction, such as reduced sensing capabilities, aphasia, flaccid limbs, paresthesia, vision and visual field loss, etc.

Because malignant brain tumor cells spread and grow within normal tissues and are not easy to eradicate with surgery, therapy for brain cancer must be assisted with chemotherapy. However, most anti-cancer drugs cannot be transmitted to brain tumor cells for cytotoxic effects due to the obstruction of the special "blood brain barrier" within the brain, and thus, the therapy effect is limited. As a result, the average lifespan of patients with terminal brain cancer is usually no more than about a year.

Currently, temozolomide (TMZ) is one of the drugs commonly used to treat malignant brain tumor in clinic. It is an imidazole-tetrazine type oral chemotherapeutic drug and can pass through the blood brain barrier to kill brain tumor cells. Therefore, it can effectively inhibit tumor proliferation and further treat brain cancer. Temozolomide is particularly effective in gliomas (including glioblastoma multiforme tumor and anaplastic astrocytoma). However, the toxicity of temozolomide is high and produces side effects such as nausea, vomiting, headache, lack of strength, fatigue, anorexia, etc. Furthermore, temozolomide is generally combined with radiation therapy to enhance the therapeutic effects, resulting in more serious side effects.

Temozolomide is a methylating agent. It is generally believed that by methylating the oxygen at the $6^{th}$ position in the guanine of DNA, temozolomide may distort the double-stranded DNA structure to inhibit DNA replication and lead to the death of cancer cells. However, such a mechanism will be inhibited by $O^6$-methylguanine DNA-methyltransferase (MGMT) in cancer cells, because MGMT will remove abnormal methylation within the cell to perform repairing functions, thus, weakening the efficacy of temozolomide. As a result, tumor cells will produce resistance to temozolomide accordingly. The aforesaid inhibition effect of MGMT makes it necessary to increase the dosage of temozolomide in order to achieve the effectiveness. This will inevitably lead to more serious side effects and increase the burden on patients.

If the temozolomide-resistance of the tumor cells can be reduced effectively, it will be possible to avoid an unnecessary increase of temozolomide dosage and reduce the burden on patients. The study has revealed that the efficacy of temozolomide is not necessarily improved when the expression of MGMT within the brain cancer patient's body is inhibited (See Ranson et. al., Randomized Trial of the Combination of Lomeguatrib and Temozolomide Compared With Temozolomide Alone in Chemotherapy Naïve Patients With Metastatic Cutaneous Melanoma, J Clin Oncol, 2007. Vol. 25:2540-5, which is incorporated hereinto by reference).

Therefore, a method for effectively reducing the resistance of brain cancer cells to temozolomide is still needed to avoid unnecessary temozolomide overdose during therapy and reduce the burden on patients. In addition, if the efficacy of temozolomide can be improved while the temozolomide-resistance of brain cancer cells is reduced, it can provide further assistance to patients during the treatment and reduce their burden.

SUMMARY

The primary objective of the present invention is to provide a method for reducing temozolomide-resistance of brain cancer cells in a subject, comprising administrating to the subject an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof:

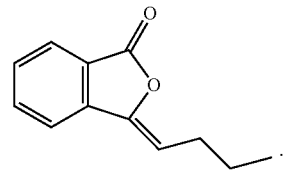

(I)

Preferably, the active ingredient is (Z)-butylidenephthalide.

Another objective of this invention is to provide a method for treating brain cancer in a subject, comprising administrating to the subject an effective amount of an active ingredient selected from the group consisting of (Z)-butylidenephthalide of aforesaid formula (I), a pharmaceutically acceptable salt of (Z)-butylidenephthalide, a pharmaceutically acceptable ester of (Z)-butylidenephthalide, and combinations thereof. Preferably, (Z)-butylidenephthalide and temozolomide are administrated to the subject.

Yet a further objective of this invention is to provide a pharmaceutical composition for reducing temozolomide-resistance of brain cancer cells, comprising a pharmaceutically acceptable carrier and an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof. Preferably, the active ingredient is (Z)-butylidenephthalide.

The present invention also provides a pharmaceutical composition for treating brain cancer, comprising a pharmaceutically acceptable carrier and an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof. Preferably, the active ingredient is (Z)-butylidenephthalide, and more preferably, the pharmaceutical composition further comprises temozolomide.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
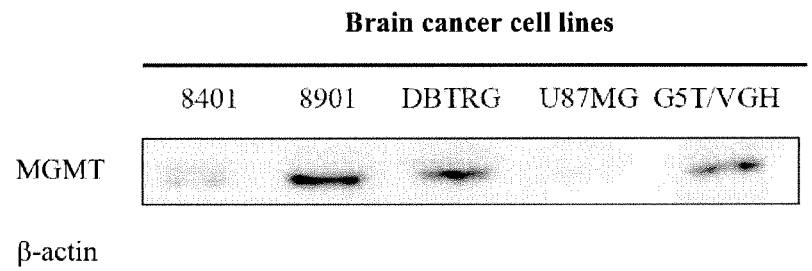
FIG. 1 is a protein electrophoresis picture showing MGMT ($O^6$-methylguanine DNA-methyltransferase) expression within various brain cancer cell lines.

Unless otherwise stated herein, the terms "a (an)", "the" or the like used in this specification (especially in the Claims hereinafter) shall be understood to encompass both the singular form and the plural form.

Brain tumors can be divided into gliomas and non-gliomas. The most commonly seen brain tumors are gliomas, which include astrocytomas (accounting for about 70% to 80% of gliomas), oligodendrogliomas, and ependymomas. Non-gliomas include embryonal tumors, meningiomas, craniopharyngiomas, schwannomas, gangliogliomas, pituitary adenomas, and choroid plexus tumors.

As mentioned above, temozolomide has high toxicity and strong side effects, and tumor cells can easily develop drug resistance to it, and therefore it is quite limited in clinical application. The inventors of the present invention found that, compared with (E)-butylidenephthalide (trans-butylidenephthalide), (Z)-butylidenephthalide (cis-butylidenephthalide) has a higher activity to inhibit MGMT expression, and can reduce temozolomide-resistance of brain tumor cells efficiently and enhance the cytotoxic sensitivity of temozolomide to temozolomide-resistant brain cancer cells. Thus, (Z)-butylidenephthalide can decrease or even solve the problems caused by administrating temozolomide to the subject.

Therefore, the present invention provides a method for reducing temozolomide-resistance of brain cancer cells in a subject, comprising administrating to the subject an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof:

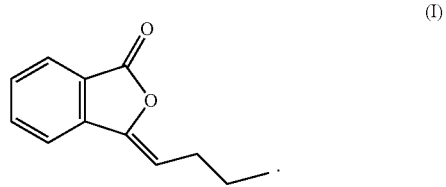

(I)

The method of the present invention is preferably used for reducing the temozolomide-resistance of human malignant glioma. Preferably, the active ingredient is (Z)-butylidenephthalide.

When applying the method of the present invention to reduce temozolomide-resistance of brain cancer cells, the active ingredient can be administrated once per day, multiple times per day, or once every few days, etc., depending on the need of the subject. For example, (Z)-butylidenephthalide can be administrated once per day, and the amount thereof is about 30 mg/kg-body weight to about 500 mg/kg-body weight. The unit "mg/kg-body weight" refers to the dosage required for the subject per kilogram of body weight. However, for patients with serious resistance to temozolomide, the dosage can be increased to several or several tens of times depending on practical conditions. Furthermore, the administration can be performed by any suitable approach, for example, but not limited thereby, oral, subcutaneous, nasal, or intravenous administration, etc. Because the drug-releasing time and dosage can be precisely controlled by injection administration, it is preferable to apply subcutaneous or intravenous injection.

It was also found that (Z)-butylidenephthalide not only can reduce the temozolomide-resistance of brain cancer cells, but also has anti-brain cancer effects, and can enhance the cytotoxicity of temozolomide to brain cancer cells. When (Z)-butylidenephthalide is administrated together with temozolomide (successively or simultaneously), (Z)-butylidenephthalide can provide excellent efficacy for brain cancer treatment and further reduce the administration dosage of temozolomide.

Therefore, the present invention also provides a method for treating brain cancer in a subject, preferably, for treating human malignant glioma in a subject. The method comprises administrating to the subject an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof. Preferably, the active ingredient is (Z)-butylidenephthalide. As illustrated in the following examples, compared to (E)-butylidenephthalide, which cannot kill brain cancer cells effectively even at a high dosage of 2500 μM, (Z)-butylidenephthalide can achieve 50% brain cancer cell death rate ($IC_{50}$) at the dosage of about 250 μM.

The method for treating brain cancer of the present invention can further comprise administrating to the subject an effective amount of an anti-cancer component selected from the group consisting of temozolomide, a hydrate of temozolomide, an isostere of temozolomide, a pharmaceutically acceptable salt of temozolomide, and combinations thereof. Preferably, the anti-cancer component is temozolomide. Preferably, the method for treating brain cancer of the present invention is carried out by administrating to the subject an effective amount of (Z)-butylidenephthalide and temozolomide to treat brain cancer with temozolomide-resistance, especially to treat human malignant glioma with temozolomide-resistance.

In the method for treating brain cancer of the present invention, when (Z)-butylidenephthalide and temozolomide are used together they can be administrated simultaneously or successively. The dosage of (Z)-butylidenephthalide and temozolomide can be optionally adjusted. It was found that in the method of the present invention, when (Z)-butylidenephthalide and temozolomide are used, under the same dosage of (Z)-butylidenephthalide, as the dosage of temozolomide increases, the combination index (CI) often decreases. The combination index is obtained by drawing the reaction curve of drug dosage and performing calculation with the CalcuSyn software (See Chou and Talalay, Quantitative analysis of dose-effect relationships: the combined effects of multiple drugs or enzyme inhibitors. *Adv. Enzyme Regul.*, 22: 27-55, 1984, which is incorporated hereinto by reference). When the combination index is less than 1, different drugs have synergism between each other and show synergistic effect on the drug efficacy. When the combination index is equal to 1, the drugs have no influence on each other. When the combination index is greater than 1, the drugs are antagonistic to each other. Preferably, in the method for treating brain cancer of the present invention, when (Z)-butylidenephthalide and temozolomide are used in combination, (Z)-butylidenephthalide and temozolomide together provide a combination index less than 1.

In one embodiment of the present invention, when the concentrations of (Z)-butylidenephthalide and temozolomide are 100 μM and 1200 μM (200 μL), respectively, the combination index is about 0.33. When the concentrations of (Z)-butylidenephthalide and temozolomide are 100 μM and 3200 μM (200 μL), respectively, the combination index is about 0.22. When the concentrations of (Z)-butylidenephthalide and temozolomide are 50 μM and 3200 μM (200 μL), respectively, the combination index is about 0.20.

Because (Z)-butylidenephthalide can effectively reduce the temozolomide-resistance of brain cancer cells, increase the cytotoxic sensitivity of temozolomide to brain cancer cells with temozolomide-resistance, and provide excellent synergistic effect when administrated together with temozolomide, it can reduce the temozolomide dosage required for the treatment and reduce the side effects caused by temozolomide administration. As illustrated in the following examples, the temozolomide dosage required to achieve 50% death rate of brain cancer cells ($IC_{50}$ value) decreases as the dosage of (Z)-butylidenephthalide increases.

In the method for treating brain cancer of the present invention, the active ingredient can be administrated with different frequencies depending on the need of the subject, such as once per day, multiple times per day, or once every few days, etc. For example, when the method is used in the human body to treat brain cancer, (Z)-butylidenephthalide can be dosed once per day (e.g., in form of a wafer or tablet) with a dosage thereof of about 30 mg/kg-body weight to about 500 mg/kg-body weight, and is preferably, about 40 mg/kg-body weight to about 120 mg/kg-body weight. The unit "mg/kg-body weight" refers to the dosage required for the subject per kilogram of body weight. When (Z)-butylidenephthalide and temozolomide are used together, temozolomide can be dosed once per day (e.g., in form of a wafer or tablet) with a dosage thereof of about 10 mg/kg-body weight to about 100 mg/kg-body weight, and preferably, about 40 mg/kg-body weight to about 80 mg/kg-body weight. For example, when (Z)-butylidenephthalide and temozolomide are used together temozolomide can be dosed once per day with a dosage of about 65 mg/kg-body weight to provide good treatment effect, wherein (Z)-butylidenephthalide and temozolomide may be contained in the same wafer or in different wafers. However, for severe brain cancer patients, the dosage can be increased by several or several tens of times depending on the conditions.

In the method for treating brain cancer of the present invention, the active ingredient (that may be combined with the anti-cancer component) can be administrated by any suitable approaches, for example, but is not limited thereto, oral, subcutaneous, nasal, or intravenous administration. The method of the present invention can be used in veterinary and human medicine, alone or in conjunction with a pharmaceutical adjuvant. When both (Z)-butylidenephthalide and temozolomide are used in the method of the present invention they can be dosed with the same or different approaches, at the same time or separately. For example, (Z)-butylidenephthalide can be administered by intravenous injection while temozolomide is administered by oral administration.

In the method for treating brain cancer of the present invention, the active ingredient (e.g., (Z)-butylidenephthalide) and the anti-cancer component (e.g., temozolomide) can be administrated together, separately, or successively. For example, (Z)-butylidenephthalide can first be dosed by injection, and after a period of time (usually 1 to 2 hours), temozolomide is dosed by an oral administration. Alternatively, after (Z)-butylidenephthalide is dosed by injection, temozolomide is dosed straight away by oral administration.

(Z)-butylidenephthalide can be obtained by any suitable approaches, for example, it can be prepared by chemical synthesis or extracted and purified from *angelica sinensis*. For instance, butylidenephthalide compounds (comprising the racemic mixtures of (Z)-butylidenephthalide and (E)-butylidenephthalide) can be purchased from the market (e.g., Alfa Aesar Company) and embedded with a suitable amount of silica gel (the weight ratio of butylidenephthalide:silica gel=1:3). Then, silica gel column chromatography is performed and n-hexane is used as the mobile phase for elution. The eluted (Z)-butylidenephthalide and (E)-butylidenephthalide are collected at different time points, and the purification result is confirmed by NMR, and (Z)-butylidenephthalide is obtained accordingly.

The present invention also provides a pharmaceutical composition for reducing temozolomide-resistance of brain cancer cells, comprising a pharmaceutically acceptable carrier and an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof. Preferably, the active ingredient is (Z)-butylidenephthalide. The application form and dosage of the active ingredient are provided in the above description for the method of the present invention.

The present invention also provides a pharmaceutical composition for treating brain cancer, comprising a pharmaceutically acceptable carrier and an effective amount of an active ingredient selected from the group consisting of (Z)-butylidenephthalide of formula (I), a pharmaceutically acceptable salt of (Z)-butylidenephthalide, a pharmaceutically acceptable ester of (Z)-butylidenephthalide, and combinations thereof. Preferably, the active ingredient is (Z)-butylidenephthalide, and more preferably, the pharmaceutical composition further comprises temozolomide. The application form and dosage of the active ingredient and the combination administration of (Z)-butylidenephthalide and temozolomide are provided in the above description for the method of the present invention.

For the dosage form suitable for oral administration, for example, the pharmaceutical composition for treating brain cancer or reducing the temozolomide-resistance of brain cancer cells of the present invention may comprise an adjuvant that would not adversely affect the efficacy of anti-brain cancer. The adjuvant can be, for example, solvents, oily solvents, diluents, stabilizers, absorption retarders, disintegrants, emulsifiers, adhesives, lubricants, moisture absorbent s, polymers, etc. For example, the solvent can be selected from water and a physiological saline solution; the polymers can be selected from polylactic acid-co-glycolic acid), collagen, hydrogel, poly-anhydride, etc.; and the poly-anhydrides can be prepared from the ingredients selected from the group consisting of bis(p-carboxylphenoxy) propane, bis(p-carboxylphenoxy) butane, bis(p-carboxylphenoxy) pentane, bis(p-carboxylphenoxy) hexane, bis(p-carboxylphenoxy) heptane, bis(p-carboxylphenoxy) octane, isophthalic acid, 1,4-phenylenedipropionic acid, dodecanedioic acid, oxalic acid, malonic acid, succinic acid, pentandioic acid, adipic acid, glutaric acid, octanedioic acid, azelaic acid, sebacic acid, phthalic acid, terephthalic acid, and combinations thereof. The pharmaceutical composition, by any known method, can be produced into any suitable oral dosage form, for example, wafers (or tablets), capsules, granules, pulvis, fluid extracts, solutions, syrups, suspensions, emulsions, tinctures, etc.

In respect to subcutaneous or intravenous dosage forms, the pharmaceutical composition for treating brain cancer or reducing temozolomide-resistance of brain cancer cells of the present invention may comprise one or more ingredients like solubilizers, emulsifiers, and other adjuvants to form an intravenous fluid injection, an intravenous emulsion injection, an injection solution, a dry powder injection, a suspension injection, a dry powder suspension injection, etc. The solvents can include water, a physiological saline solution, alcohols (for example, ethanol, propanol, or glycerol, etc), a sugar solution, or combinations thereof.

The pharmaceutical composition for treating brain cancer or reducing temozolomide-resistance of brain cancer cells of the present invention can optionally further comprise additives such as flavoring agents, toners, coloring agents, etc, to improve the oral and visual sensations during administration. Yet, a reasonable amount of preservatives, anti-microbial agents, anti-fungal agents, etc, can be added to improve the storability of the medicament.

The pharmaceutical composition for treating brain cancer or reducing temozolomide-resistance of brain cancer cells of the present invention can optionally further comprise one or more anti-brain cancer ingredients to enhance the efficacy of the pharmaceutical composition of the present invention or increase the flexibility for manufacturing formulations, as long as other anti-cancer ingredients do not have adverse effects on the efficacy of (Z)-butylidenephthalide and/or temozolomide.

The detailed technology and preferred embodiments implemented for the present invention are described in the following paragraphs accompanying the appended drawings for people skilled in this field to well appreciate the features of the claimed invention.

EXAMPLES

Example 1

MGMT Expression in Different Brain Cancer Cell Lines

The brain cancer cell lines 8401, 8901, DBTRG, U87MG, and G5T/VGH were cultured in a petri dish with a diameter of 10 cm, respectively. A phosphate buffer saline (PBS) solution was used to rinse the cells after the cell proliferation reached to 60% by volume of the dish. Finally, the cells and intracellular proteins were collected. Sodium dodecyl sulfate-polyacrylamide gel electrophoresis (SDS-PAGE) and western blotting were used to analyze the expression of the MGMT protein in each brain cancer cell line. The results are shown in FIG. 1.

As shown in FIG. 1, each brain cancer cell line showed different levels of MGMT expression, and the brain cancer cell line 8901, DBTRG, and G5T/VGH had higher levels of MGMT expression.

Example 2

The Mortality Effect of Temozolomide to Various Brain Cancer Cell Lines

The MTT (3-[4,5-dimethylthiahiazo-2-yl]-2,4-diphenytetrazolium bromide) cell viability assay was used to study the mortality effect of temozolomide to various brain cancer cell lines. (See Pauwels et al., *J. Virol. Methods,* 1988, 20, 309-321 for the MTT cell viability assay, which is incorporated hereinto by reference).

In a 96-microwell plate, each well was respectively cultured with $3 \times 10^3$ brain cancer cell lines 8401, 8901, DBTRG, U87MG, and G5T/VGH. Next day, different concentrations of temozolomide (0 to 3200 μM, 200 μL) were dropped into the well along the interior wall of the plate. A solvent was placed into the first row as the control group. After the cells were cultured for 2 days, the culture solution was drew and discarded, and a culture solution containing 500 μg/mL of MTT (200 μL) was added to culture for another 4 hours. The culture solution was drew and discarded, 200 μL of DMSO was added, and then a microwell plate spectrometer was used to measure the absorbance of the cells at a wavelength of 570 nm. The cell viability rate, mortality rate, and concentrations of temozolomide that reached a 50% mortality rate of various brain cancer cell lines ($IC_{50}$) were calculated based on the absorbance. The above experiment results are shown in Table 1 and FIG. 2.

TABLE 1

| Brain cancer cell line | IC$_{50}$ value (μM) |
|---|---|
| DBTRG | 1658.6 |
| 8401 | 831.3 |
| 8901 | 1201.6 |
| G5T/VGH | 1660.1 |

Figure 2:
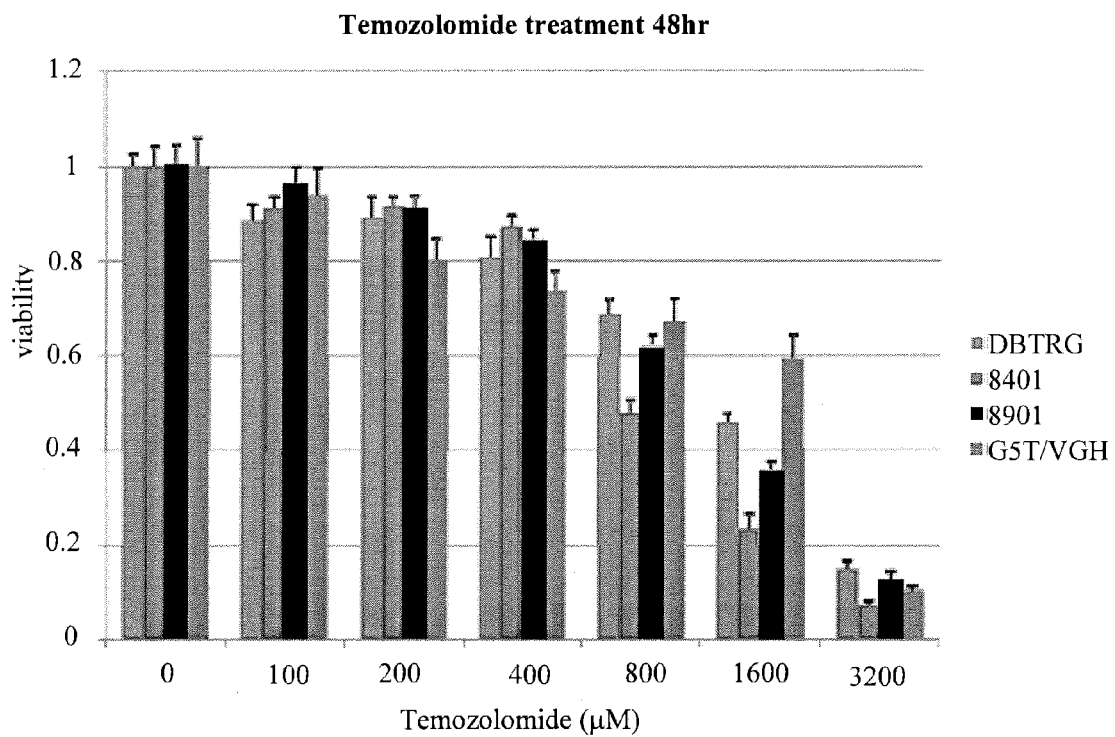
FIG. 2 is a statistical bar diagram showing the inhibition rate of temozolomide to various brain cancer cell lines.

As shown in Table 1 and FIG. 2, compared with brain cancer cell line 8401, brain cancer cell lines 8901, DBTRG, and G5T/VGH with high MGMT expression level showed higher IC$_{50}$ values of temozolomide, indicating that brain cancer cell lines with high MGMT expression have drug-resistance to temozolomide, thus requiring a higher dosage to achieve the mortality effect.

Example 3

The Inhibition of Butylidenephthalide to the MGMT Expression in Brain Cancer Cells This experiment showed the inhibitory effect of (Z)-butylidenephthalide and (E)-butylidenephthalide to the MGMT expression in brain cancer cells.

Brain cancer cell lines 8901 and GBM22-TMZ with temozolomide-resistance were cultured in a petri dish with a diameter of 10 cm, respectively. A PBS solution was used to rinse the cells after the cell proliferation reached to 60% by volume of the dish. (Z)-butylidenephthalide or (E)-butylidenephthalide was added to treat the cells for 3 to 48 hours, and then the cells were collected. The total RNA of the cells was extracted and reverse transcribed into cDNA (using 50 micro-mole of oligo dNTP and 50 pico-mole of random hexamers primer). One unit of ExTaq DNA polymerase, 200 nM dNTP (1 μL), and 2.5 mM of MgCl$_2$ (1 μL) were added, and then 20 mM of MGMT nucleotide primers (1 μL each) and 50 μL of water were added.

The sample was placed into a polymerase chain reaction (PCR) system (GeneAmp PCR System 2400, Perkin Elmer, USA). The condition was set as: denaturing, 94° C., 30 s; annealing, 55° C., 30 s; extension, 94° C., 60 s; 30 cycles; and finally 72° C., 10 minutes. Afterwards, the system temperature was decreased to 4° C. to terminate the reaction. The product from the PCR was analysed by a 1.5% gel electrophoresis. The gel was analysed by Fluoro-Chem imaging system (Alpha InnoTech Cooperation) to determine the expression level of MGMT gene. The result is shown in FIG. 3.

In another aspect, the intracellular proteins of the aforesaid brain cancer cell lines 8901 and GBM22-TMZ were collected. SDS-PAGE and western blotting were used to analyze the expression of the MGMT protein in the brain cancer cell lines. The results are shown in FIGS. 4 and 5.

Figure 3:
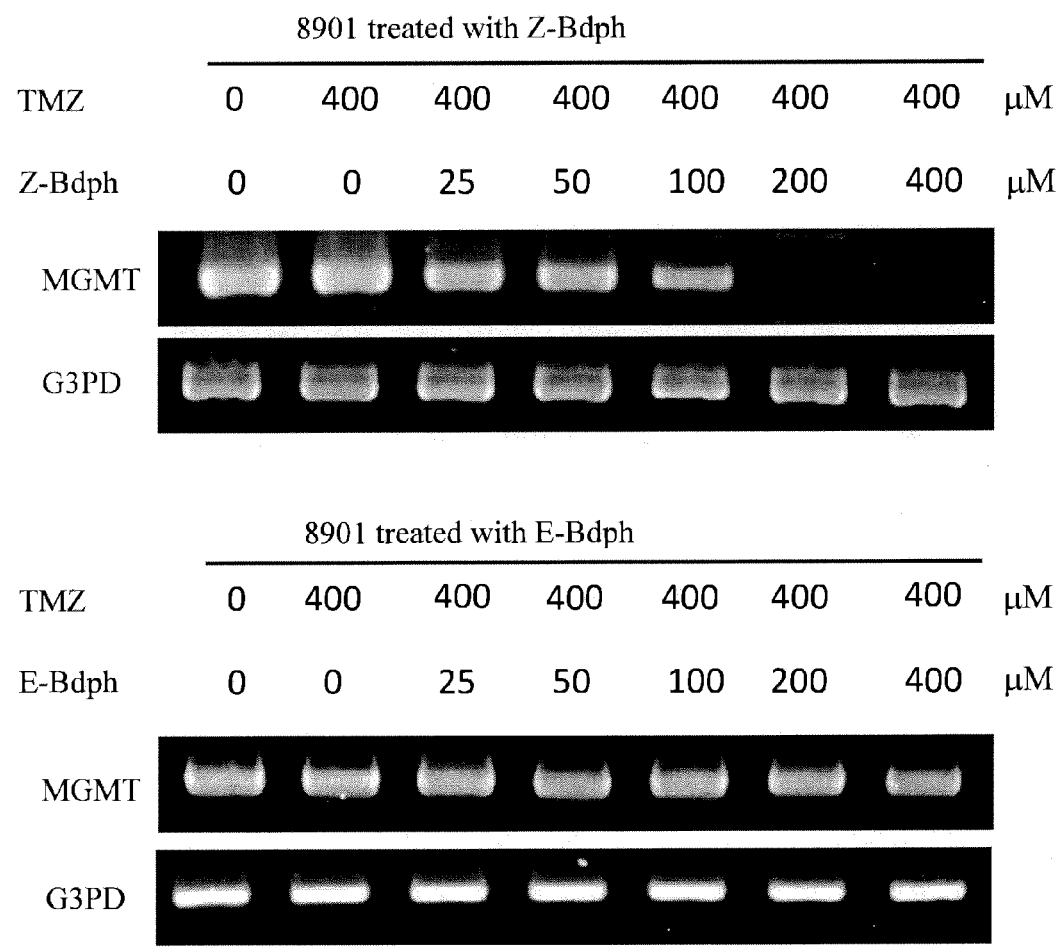
FIG. 3 is an electrophoresis picture showing the influence of (Z)-butylidenephthalide (Z-Bdph) and (E)-butylidenephthalide (E-Bdph) on the RNA expression of MGMT in brain cancer cell line 8901.
Figure 4:
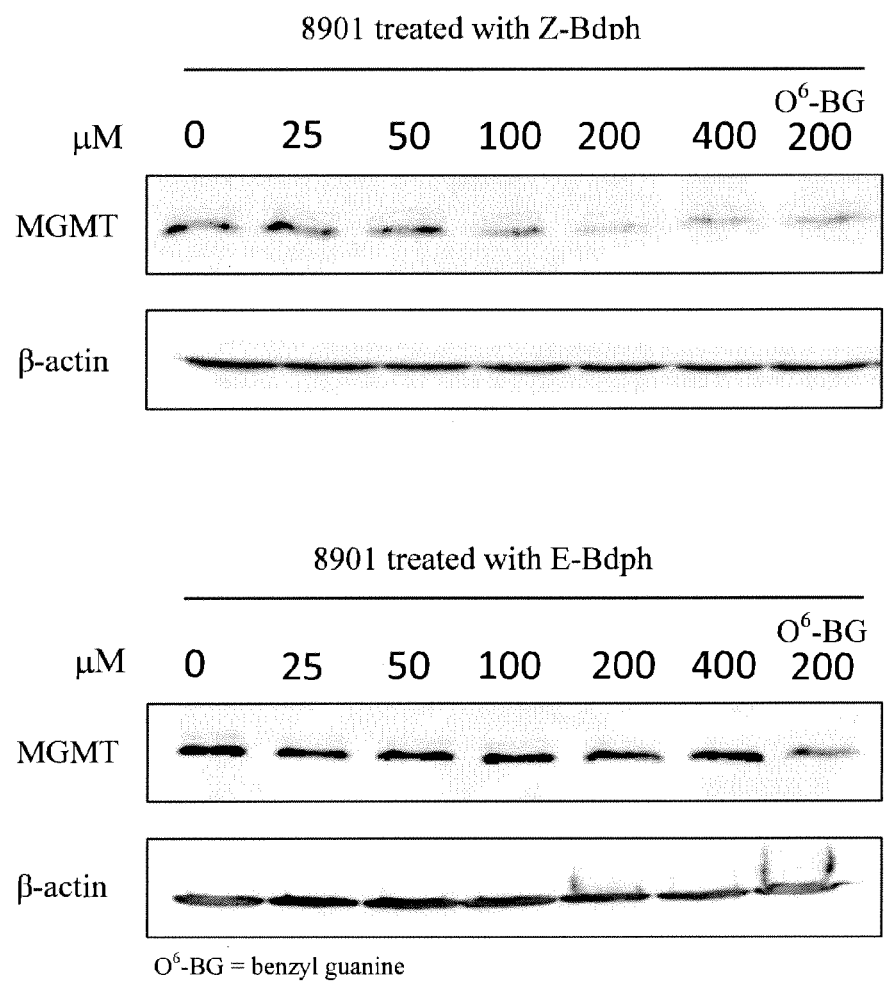
FIG. 4 is a protein electrophoresis picture showing the influence of (Z)-butylidenephthalide and (E)-butylidenephthalide on the protein expression of MGMT in the temozolomide-resistant brain cancer cell line 8901.
Figure 5:
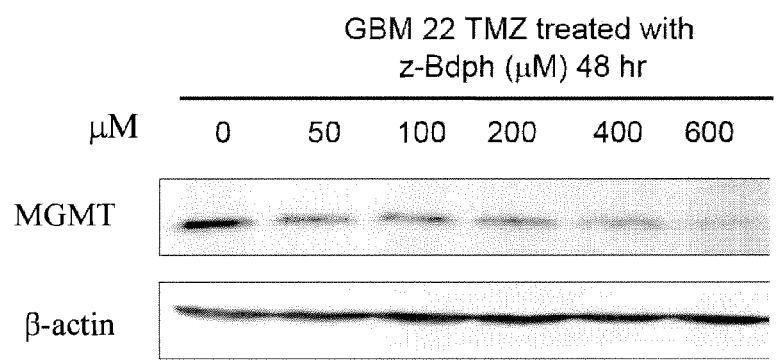
FIG. 5 is a protein electrophoresis picture showing the inhibition of (Z)-butylidenephthalide on the protein expression of MGMT in the temozolomide-resistant brain cancer cell line GBM22-TMZ.

As shown in FIGS. 3 to 5, the expression of RNA and proteins of MGMT within the brain cancer cell lines were reduced while the concentration of (Z)-butylidenephthalide increased, indicating that (Z)-butylidenephthalide can inhibit the expression of MGMT. However, there were no significant changes for the expression of RNA and proteins of MGMT within the brain cancer cell lines as the concentration of (E)-butylidenephthalide increased.

Example 4

(Z)-Butylidenephthalide Increases the Cytotoxic Sensitivity of Temozolomide to the Brain Cancer Cell Line 8901

The MTT cell viability assay was used to test if (Z)-butylidenephthalide can increase the cytotoxic sensitivity of temozolomide to the brain cancer cells.

In a 96-microwell plate, each well was cultured with $3 \times 10^3$ cells of brain cancer cell line 8901 which have temozolomide-resistance. The next day, different concentrations of temozolomide (0 to 1200 μM, 200 μL) or the combination of temozolomide and (Z)-butylidenephthalide (0 to 200 μM, 200 μL) were dropped into the well along the interior wall of the plate. Four microwell plates were used for each analysis, and four wells were used for each combination of various drug concentrations. A solvent was placed into the first row as the control group. After the cells were cultured for 2 days, the culture solution was drawn and discarded, and a culture solution containing 500 μg/mL of MTT (200 μL) was added to culture for another 4 hours. The culture solution was drawn and discarded, and 200 μL of DMSO was added, and then the microwell plate spectrometer was used to measure the absorbance of the cells at a wavelength of 570 nm. The cell viability rate and mortality rate and the concentrations of temozolomide that reached the mortality rate of 50% of various brain cancer cell lines (IC$_{50}$) were calculated based on the absorbance. The above experiment results are shown in Table 2 and FIG. 6.

TABLE 2

| Brain cancer cell line 8901 | |
|---|---|
| Active ingredient | IC$_{50}$ (μM) |
| Temozolomide | 1201.6 |
| Temozolomide + (Z)-butylidenephthalide (25 μM) | 992.3 |
| Temozolomide + (Z)-butylidenephthalide (50 μM) | 866.8 |
| Temozolomide + (Z)-butylidenephthalide (100 μM) | 685.5 |
| Temozolomide + (Z)-butylidenephthalide (200 μM) | 582.5 |

Figure 6:
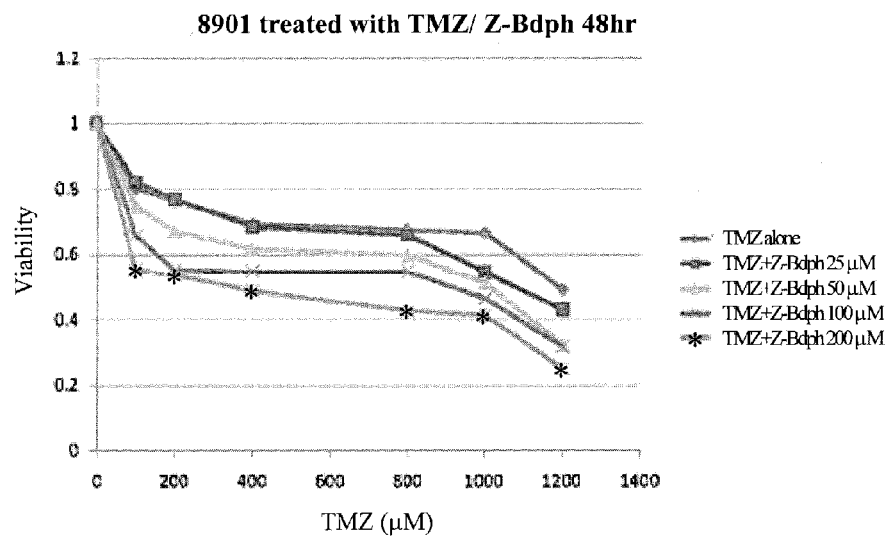
FIG. 6 is a curve diagram showing the inhibition rate of the combination of (Z)-butylidenephthalide and temozolomide to the temozolomide-resistant brain cancer cell line 8901.

As shown in Table 2 and FIG. 6, when the combination of (Z)-butylidenephthalide and temozolomide was used, the temozolomide dosage required to reach the mortality rate of 50% of brain cancer cell lines (IC$_{50}$) reduced as the dosage of (Z)-butylidenephthalide increased, indicating that (Z)-butylidenephthalide can increase the cytotoxic sensitivity of temozolomide to the brain cancer cell line. Thus, the dosage of temozolomide can be reduced when the combination of (Z)-butylidenephthalide and temozolomide is used.

Example 5

(Z)-Butylidenephthalide Increases the Cytotoxic Sensitivity of Temozolomide to the Brain Cancer Cell Line GBM22-TMZ The experiment steps in Example 4 were repeated, but the brain cancer cell line was changed to temozolomide-resistant GBM22-TMZ, and the concentration of temozolomide was changed from 0 to 3200 μM (200 μL), while the concentration of (Z)-butylidenephthalide was changed from 0 to 600 μM (200 μL). The result is shown in FIG. 7.

Figure 7:
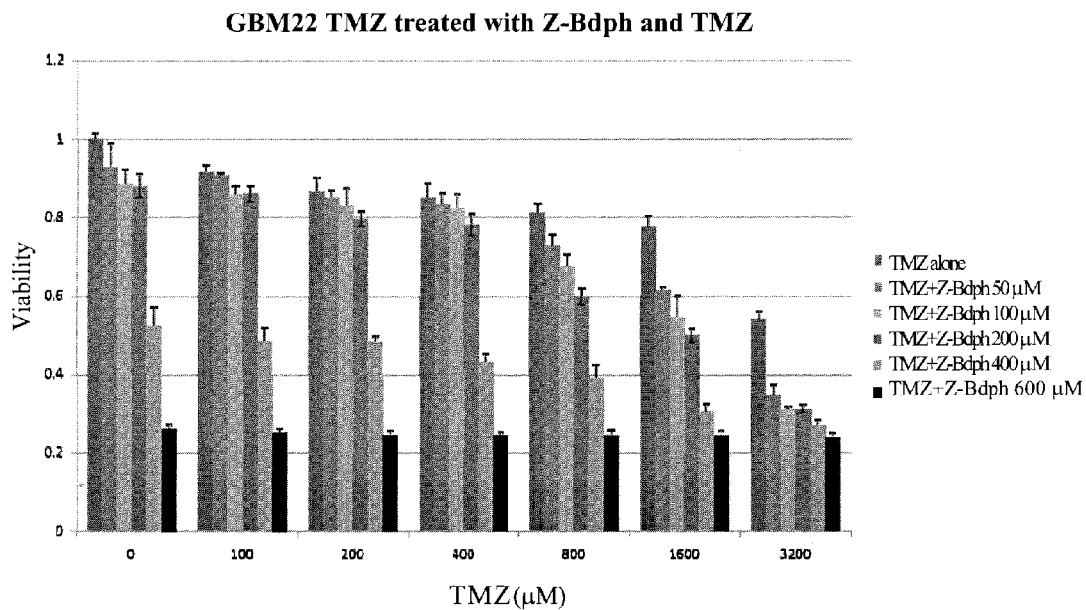
FIG. 7 is a statistical bar diagram showing the inhibition rate of the combination of (Z)-butylidenephthalide and temozolomide to the brain cancer cell line GBM22-TMZ.

As shown in FIG. 7, when the combination of (Z)-butylidenephthalide and temozolomide was used, the killing effect of temozolomide to the brain cancer cell line improved as the dosage of (Z)-butylidenephthalide increased, indicating that (Z)-butylidenephthalide can increase the cytotoxic sensitivity of temozolomide to the brain cancer cell line, and thus, the dosage of temozolomide can be reduced when the combination of (Z)-butylidenephthalide and temozolomide is used.

Example 6

Inhibition Test of Butylidenephthalide on Brain Cancer Cells

The MTT cell viability assay was used to study the anti-brain cancer activity of (Z)-butylidenephthalide and (E)-butylidenephthalide.

In a 96-microwell plate, each well was cultured with $3 \times 10^3$ cells of brain cancer cell line DBTRG. The next day, different concentrations of (Z)-butylidenephthalide (0 to 500 μM, 200 μL) or (E)-butylidenephthalide (0 to 2500 μM, 200 μL) were dropped into the well along the interior wall of the plate. A solvent was placed into the first row as the control group. After the cells were cultured for 2 days, the culture solution was drawn and discarded. A culture solution containing 500 μg/mL of MTT (200 μL) was added to culture for another 4 hours. The culture solution was drawn and discarded, and 200 μL of DMSO was added, and then the microwell plate spectrometer was used to measure the absorbance of the cells at a wavelength of 570 nm. The cell viability rate and mortality rate were calculated based on the absorbance. The results are shown in Table 3 and FIGS. 8 and 9.

TABLE 3

| | (Z)-butylidenephthalide | | | | (E)-butylidenephthalide | | | |
|---|---|---|---|---|---|---|---|---|
| Concentration (μM) | 0 | 125 | 250 | 500 | 0 | 500 | 1500 | 2500 |
| Viability rate of DBTRG(%) | 100 | 80 | 58 | 30 | 100 | 88 | 81 | 70 |

Figure 8:
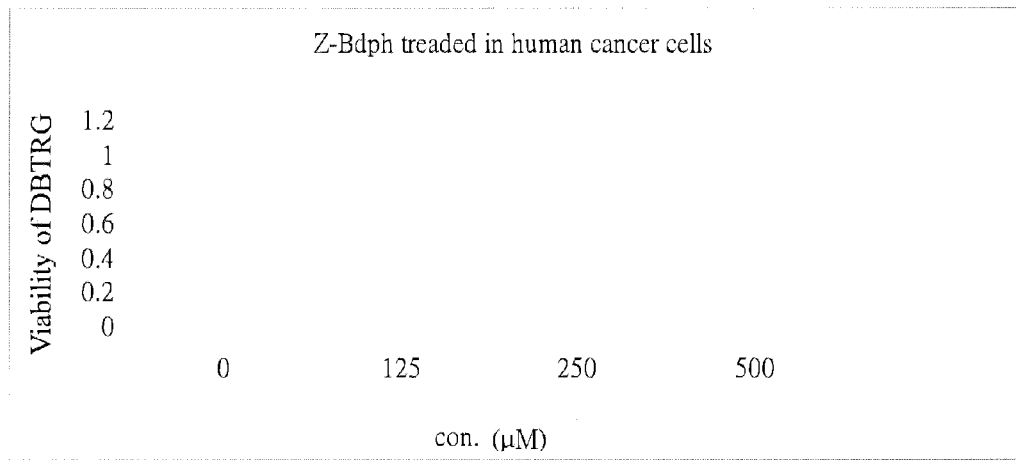
FIG. 8 is a curve diagram showing the inhibition rate of (Z)-butylidenephthalide to the brain cancer cell line DBTRG.
Figure 9:
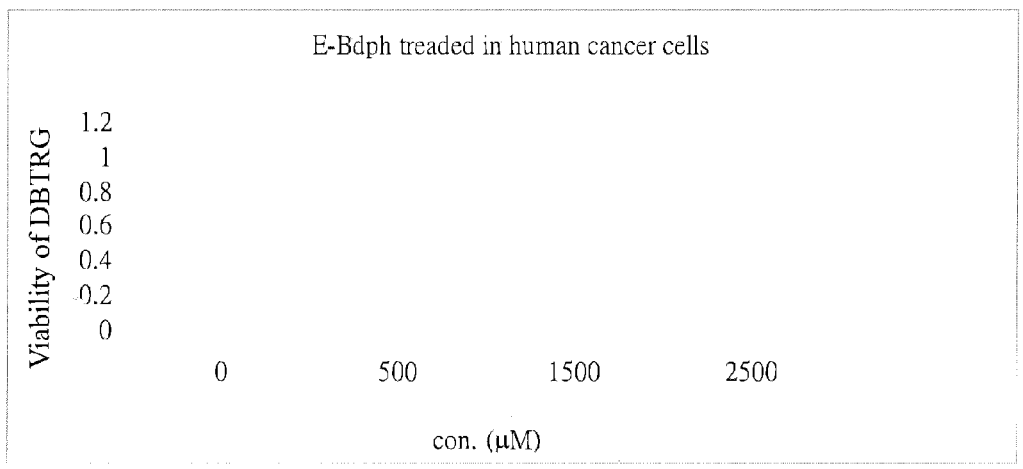
FIG. 9 is a curve diagram showing the inhibition rate of (E)-butylidenephthalide to the brain cancer cell line DBTRG.

As shown in Table 3 and FIGS. 8 and 9, compared with (E)-butylidenephthalide, which cannot kill brain cancer cells effectively even at a high dosage with the concentration of 2500 μM, (Z)-butylidenephthalide can reach the mortality rate of 50% of the cancer cells at the dosage concentration of about 250 μM.

Example 7

Inhibition Test of (Z)-Butylidenephthalide on Brain Cancer Cells

The experiment steps in Example 6 were repeated, but the cancer cell lines were replaced by brain cancer cell lines DBTRG, 8401, 8901, and G5T/VGH, and the concentration of (Z)-butylidenephthalide was changed from 0 to 400 μM (200 μL). The result is shown in FIG. 10.

Figure 10:
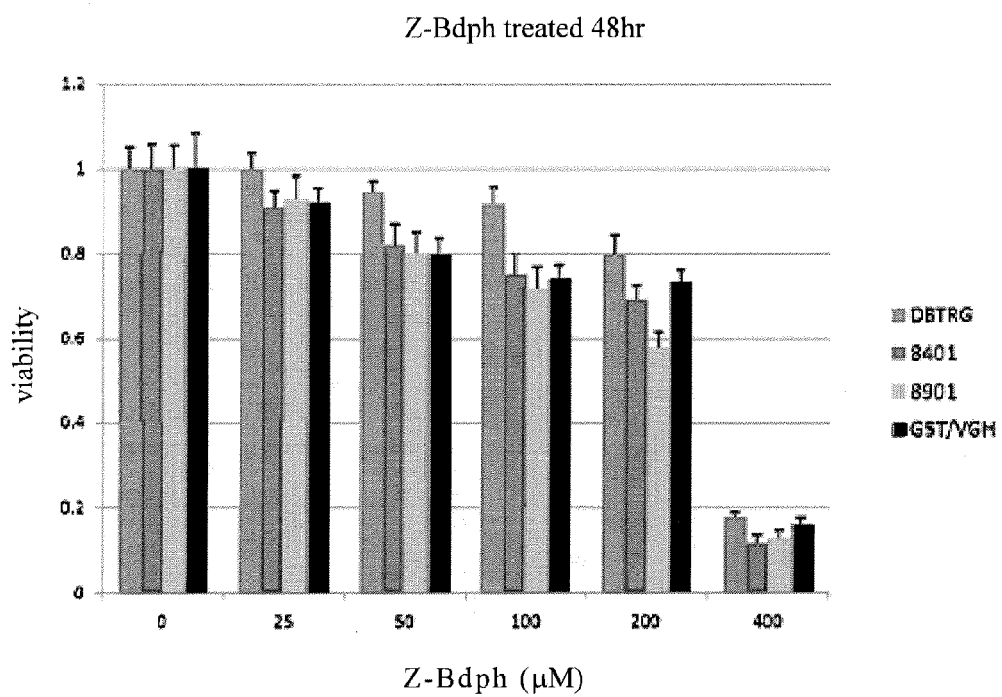
FIG. 10 is a statistical bar diagram showing the inhibition rate of (Z)-butylidenephthalide to various brain cancer cell lines.

As shown in FIG. 10, (Z)-butylidenephthalide can effectively inhibit the growth of various brain cancer cell lines, and as the dosage is increased, the effect of inhibiting brain cancer cells improves.

Example 8

The Synergistic Effect of the Composition of (Z)-Butylidenephthalide and Temozolomide to Inhibit Brain Cancer Cells The MTT cell viability assay was used to study the activity of the combination of different concentrations of (Z)-butylidenephthalide and temozolomide on anti-brain cancer cells. The combination index (CI) was analysed to see if there was any synergistic effect between (Z)-butylidenephthalide and temozolomide.

In a 96-microwell plate, each well was cultured with $3 \times 10^3$ cells of brain cancer cell line 8901 or GBM22-TMZ with temozolomide-resistance. The next day, different concentrations of (Z)-butylidenephthalide (brain cancer cell line 8901: 25 to 200 μM (200 μL), brain cancer cell line GBM22-TMZ: 50 to 600 μM (200 μL), temozolomide (brain cancer cell line 8901: 100 to 1200 μM (200 μL), brain cancer cell line GBM22-TMZ: 100 to 3200 μM (200 μL)) were dropped into the well along the interior wall of the plate. Four microwell plates were used for each analysis, and four wells were used for each combination of various drug concentrations. A solvent was placed into the first row as the control group. After the cells were cultured for 2 days, the culture solution was drawn and discarded, and a culture solution containing 500 μg/mL of MTT (200 μL) was added to culture for another 4 hours. The culture solution was drawn and discarded and then 200 μL of DMSO was added. The microwell plate spectrometer was then used to measure the absorbance of the cells at a wavelength of 570 nm. The O.D. average values of the combinations of various drug concentrations can be used to calculate and draw the reaction curve for different drug dosages. The reading of the well with the highest drug dosage was used as the positive control (that is, the growth of living cells was not inhibited), while the reading of the wells of the first row that only has the solvent added was used as the negative control, thereby, obtaining the $IC_{50}$ values of the drugs.

In addition, the CalcuSyn software was used to draw the reaction curve for drug dosages, and the combination index was calculated to analyze the pharmaceutical composition of (Z)-butylidenephthalide and temozolomide and their synergism, additivity, or antagonism (see Chou and Talalay, Quantitative analysis of dose-effect relationships: the combined effects of multiple drugs or enzyme inhibitors. *Adv. Enzyme Regul.*, 22:27-55, 1984, which is incorporated hereinto by reference). When the combination index is less than 1, (Z)-butylidenephthalide and temozolomide have synergism between each other, which means that the drug efficacy has a synergistic effect. When the combination index is equal to 1, there is no influence between (Z)-butylidenephthalide and temozolomide. When the combination index is greater than 1, (Z)-butylidenephthalide and temozolomide are antagonistic to each other. The results are shown in Tables 4, 5, and 6.

TABLE 4

| | $IC_{50}$ (μM) | |
|---|---|---|
| Active ingredient | 8901 | GBM22-TMZ |
| (Z)-butylidenephthalide | 218.62 | 450.9 |
| Temozolomide | 1201.6 | >3200 |

TABLE 5

| Brain cancer cell line 8901 | | |
|---|---|---|
| (Z)-butylidenephthalide (μM) | Temozolomide (μM) | CI Value |
| 25 | 100 | 1.777 |
| | 200 | 1.708 |
| | 400 | 1.361 |
| | 1000 | 0.950 |
| | 1200 | 0.455 |

TABLE 5-continued

Brain cancer cell line 8901

| (Z)-butylidenephthalide (μM) | Temozolomide (μM) | CI Value |
|---|---|---|
| 50 | 100 | 1.017 |
|  | 200 | 0.841 |
|  | 400 | 0.902 |
|  | 1000 | 0.839 |
|  | 1200 | 0.242 |
| 100 | 100 | 0.846 |
|  | 200 | 0.610 |
|  | 400 | 0.776 |
|  | 1000 | 0.748 |
|  | 1200 | 0.332 |
| 200 | 100 | 0.951 |
|  | 200 | 0.991 |
|  | 400 | 0.922 |
|  | 800 | 0.822 |
|  | 1000 | 0.827 |
|  | 1200 | 0.369 |

TABLE 6

Brain cancer cell line GBM22-TMZ

| (Z)-butylidenephthalide (μM) | Temozolomide (μM) | CI Value |
|---|---|---|
| 50 | 100 | 1.713 |
|  | 200 | 1.168 |
|  | 400 | 1.438 |
|  | 800 | 0.894 |
|  | 1600 | 0.649 |
|  | 3200 | 0.198 |
| 100 | 100 | 1.578 |
|  | 400 | 1.776 |
|  | 800 | 0.881 |
|  | 1600 | 0.581 |
|  | 3200 | 0.223 |
| 200 | 100 | 2.911 |
|  | 200 | 2.898 |
|  | 400 | 2.105 |
|  | 800 | 0.961 |
|  | 1600 | 0.725 |
|  | 3200 | 0.359 |
| 400 | 100 | 1.026 |
|  | 200 | 1.176 |
|  | 400 | 0.872 |
|  | 800 | 0.776 |
|  | 1600 | 0.513 |
|  | 3200 | 0.569 |
| 600 | 100 | 0.622 |
|  | 200 | 0.601 |
|  | 400 | 0.604 |
|  | 800 | 0.619 |
|  | 1600 | 0.622 |
|  | 3200 | 0.632 |

As shown in Tables 5 and 6, when (Z)-butylidenephthalide and temozolomide were used together, this combination could provide a combination index less than 1 (shown as the black bold numerical values in the tables). Under such conditions, (Z)-butylidenephthalide and temozolomide had synergistic efficacy between each other. In particular, when the concentrations of (Z)-butylidenephthalide and temozolomide were 100 μM and 1200 μM (200 μL), respectively, the combination index was about 0.33. When the concentrations of (Z)-butylidenephthalide and temozolomide were 100 μM and 3200 μM (200 μL), respectively, the combination index was about 0.22. When the concentrations of (Z)-butylidenephthalide and temozolomide were 50 μM and 3200 μM (200 μL), respectively, the combination index was about 0.20.

The test shows that (Z)-butylidenephthalide and temozolomide can provide excellent synergistic efficacy when they are used together.

Example 9

In Vivo Test

An in vivo test was carried out by a subcutaneous tumor transplant mode to observe the anti-tumor activity of (Z)-butylidenephthalide, temozolomide, or their combination in vivo.

First, $2 \times 10^6$ cells of brain cancer cell line GBM22-TMZ with temozolomide-resistance were cultured sterilely and subcutaneously injected to Balb/c nude mice (purchased from the National Laboratory Animal Center, Taiwan) to carry out the in vivo tumor transplant experiment. When the tumor was grown to 100 mm$^3$ (length×width×width/2), the subcutaneous administration was carried out for treatment. On the contralateral side of the tumor tissue, at a position more than 1.5 cm, (Z)-butylidenephthalide was injected, or temozolomide was orally administrated, once per day consecutively for 5 days. In the treatment group in which (Z)-butylidenephthalide and temozolomide were administrated in combination, (Z)-butylidenephthalide was first subcutaneously administrated (SC), and 2 hours later, temozolomide was orally administrated (PO). After administration on the 5$^{th}$ day, the tumor size and the body weight of the mice were observed continuously for 28 days, and were measured every 3 days. The measurement value of the tumor size on the 28$^{th}$ day was used as the assessment result of the inhibiting activity on tumor growth. The smaller the value, the better the inhibition effect. The relative tumor size between the group with the treatment of drugs separately or in combination and the control group (only with solvent injection) was observed to see if there was any significant difference. There was a significant difference when P value was less than 0.5. The results are shown in Table 7, and FIGS. 11A and 11B.

TABLE 7

| Medicament | Treatment mode/Time | Dosage (mg/kg/day) | Relative tumor size (fold) | Statistical analysis |
|---|---|---|---|---|
| solvent | Sc/consecutively for 5 days | 0 | 4.9 |  |
| temozolomide | PO/consecutively for 5 days | 66 | 4.3 | P = 0.85 |
| (Z)-butylidenephthalide | SC/consecutively for 5 days | 50 | 2.7 | P = 0.52 |
| (Z)-butylidenephthalide | SC/consecutively for 5 days | 100 | 2.6 | P = 0.44 |
| (Z)-butylidenephthalide + temozolomide | SC/consecutively for 5 days + PO/consecutively for 5 days | 50 + 66 | 1.3 | P = 0.13 |
| (Z)-butylidenephthalide + temozolomide | SC/consecutively for 5 days + PO/consecutively for 5 days | 100 + 66 | 1.5 | P = 0.26 |

Figure 11A:
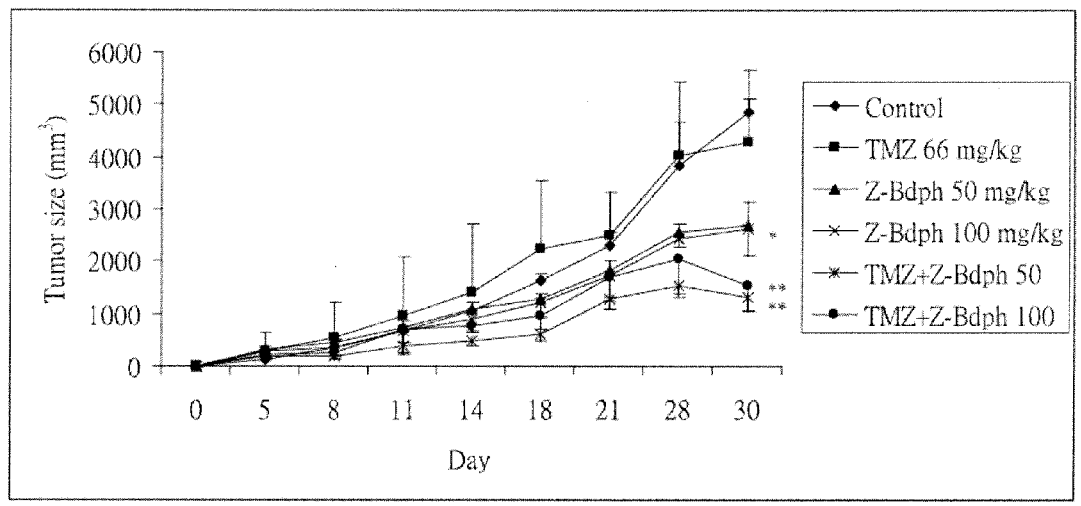
FIG. 11A is a curve diagram showing the inhibition of tumor growth within the mouse by (Z)-butylidenephthalide, temozolomide, or the combination thereof.
Figure 11B:
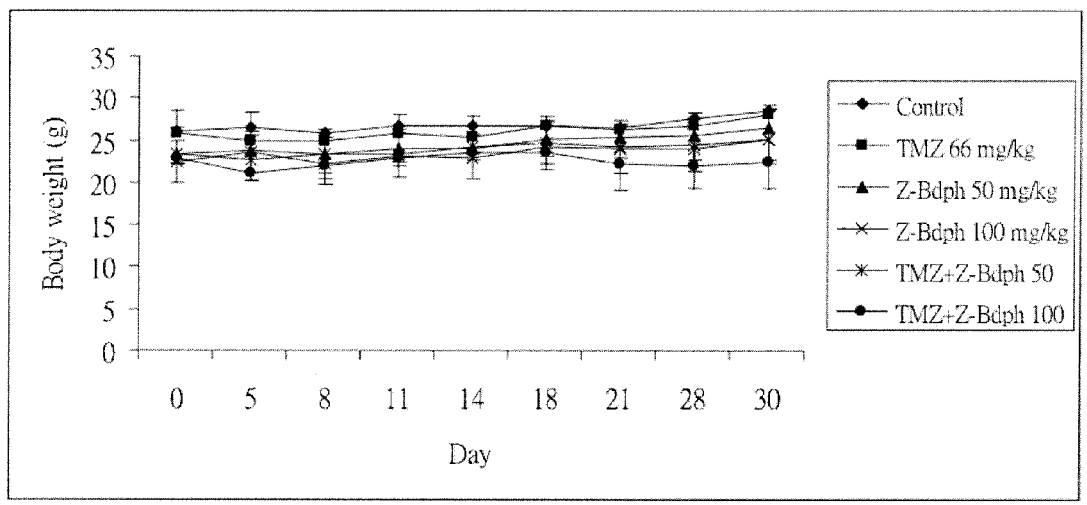
FIG. 11B is a curve diagram showing the variation of the mouse body weight.

As shown in Table 7 and FIG. 11A, compared with the separate administration of (Z)-butylidenephthalide or temozolomide, the combination administration of (Z)-butylidenephthalide and temozolomide with the same dosage could inhibit the tumor growth even more effectively. This in vivo test illustrated that (Z)-butylidenephthalide and temozolomide are synergistic with each other, and the combination of (Z)-butylidenephthalide and temozolomide could provide a more excellent treating effect for brain cancer, and reduce the dosage of (Z)-butylidenephthalide and temozolomide required for the treatment.

Example 10

In Vivo Test—Wafer Formulation Test (Z)-butylidenephthalide and polylactic acid-co-glycolic acid) (p(CPP-co-SA)) were mixed evenly by a physical method. The resultant mixed powder was placed into a round mold with a diameter of 1 to 13 mm and pressed to form a round wafer (or tablet) with a thickness of 1 to 2 mm. Dichloromethane (10% w/v) was used to mix temozolomide and p(CPP-co-SA), and dichloromethane was then evaporated by a vacuum pump, and finally, the resultant powder was pressed to form a round wafer (or tablet) to prepare a temozolomide wafer.

Female BALB/c nu/nu mice, 6 to 8 weeks old, weighted between 18 to 22 g (purchased from the National Laboratory Animal Center, Taiwan) were used to carry out the transplant of temozolomide-resistant human brain cancer cell line to evaluate the anti-cancer effect of (Z)-butylidenephthalide, temozolomide, or their combination. $2 \times 10^6$ brain cancer cell line GBM22-TMZ were implanted subcutaneously to the mice. The treatment was carried out when the tumor formed and grew to 100 to 300 mm$^3$. The mice were randomly grouped. There were 6 to 8 mice each in the control group (without treatment by the wafers) and in the treatment group (with treatment by the wafers). The wafers with different dosage combination ((Z)-butylidenephthalide:temozolomide=1:2 or 1:4) were implanted subcutaneously 1 cm away from the tumor tissue, and the variation of the tumor size and the body weight of the mice was measured and recorded every 2 days. The experimental results are shown in FIGS. 12A and 12B.

Figure 12A:
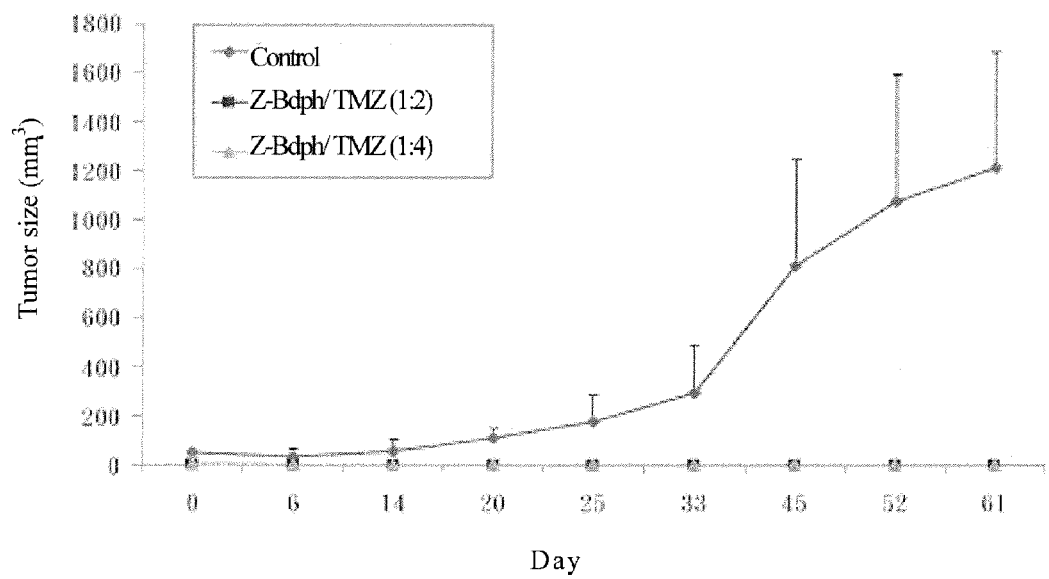
FIG. 12A is a curve diagram showing the inhibition of tumor growth within the mouse by combining the (Z)-butylidenephthalide wafer (or tablet) and temozolomide wafer (or tablet)
Figure 12B:
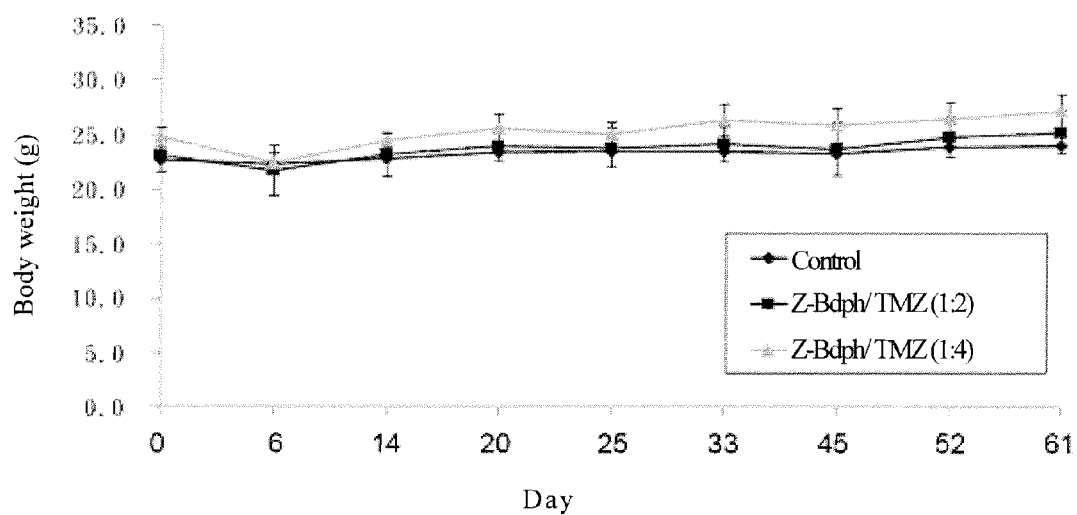
FIG. 12B is a curve diagram showing the variation of the mouse body weight.

As shown in FIG. 12A, the tumor growth could be effectively inhibited when the combination of the (Z)-butylidenephthalide wafer and the temozolomide wafer was used.

The above examples show that (Z)-butylidenephthalide can effectively reduce the temozolomide-resistance of brain cancer cells, and it can provide excellent synergism effect when used in combination with temozolomide. Therefore, the dosage of temozolomide required for the treatment can be reduced, and the side effects caused by the administration of temozolomide can also be reduced.

Example 11

In Vivo Test—Survival Analysis

A survival analysis was carried out to investigate the antiglioma effect of the combination of (Z)-butylidenephthalide and temozolomide in vivo. Mice with established glioblastoma orthotopic xenografts from brain cancer cell line GBM22-TMZ were randomized to carry out the therapy with indicated temozolomide (66 mg/kg/day; 5 days), (Z)-butylidenephthalide (50 or 100 mg/kg/day; 5 days), or combinations thereof. Observation was recorded until the mice reached a moribund state, and survival results are shown as Kaplan-Meier survival curves. The survival rate is shown in Table 8.

TABLE 8

| Survival rate | Day | | | | | | | | |
| --- | --- | --- | --- | --- | --- | --- | --- | --- | --- |
| | 0 | 5 | 8 | 11 | 14 | 18 | 21 | 28 | 30 |
| Control | 100 | 100 | 100 | 100 | 100 | 100 | 25 | 0 | 0 |
| temozolomide (66 mg/kg) | 100 | 100 | 100 | 66 | 66 | 66 | 33 | 0 | 0 |
| (Z)-butylidenephthalide (50 mg/kg) | 100 | 100 | 100 | 100 | 100 | 100 | 66 | 0 | 0 |
| (Z)-butylidenephthalide (100 mg/kg) | 100 | 100 | 100 | 100 | 100 | 100 | 66 | 0 | 0 |
| (Z)-butylidenephthalide (66 mg/kg) + temozolomide (50 mg/kg) | 100 | 100 | 100 | 100 | 100 | 100 | 100 | 100 | 100 |
| (Z)-butylidenephthalide (66 mg/kg) + temozolomide (100 mg/kg) | 100 | 100 | 100 | 100 | 100 | 100 | 100 | 100 | 100 |

$P < 0.05$

As shown in Table 8, compared with the control group, mice treated with temozolomide, (Z)-butylidenephthalide, or the combination thereof displayed improved survival rate. In addition, the mice treated with temozolomide along with (Z)-butylidenephthalide (50 mg/kg or 100 mg/kg) showed the survival rate of 100%, indicating that the survival rate of the mice having tumor could be effectively improved when the combination of (Z)-butylidenephthalide and temozolomide was used.

This survival analysis showed that (Z)-butylidenephthalide can provide excellent synergism effect when used in combination with temozolomide. Therefore, the dosage of temozolomide required for the cancer treatment can be reduced, and the side effects caused by the administration of temozolomide can also be reduced.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for treating a glioma in a subject, comprising:
administering to the subject (1) an effective amount of the (Z)-butylidenephthalide isomer of formula (I) substantially free from the (E)-butylidenephthalide isomer of formula (I), wherein the (Z)-butylidenephthalide isomer of formula (I) is in the form of the (Z)-butylidenephthalide isomer, a pharmaceutically acceptable salt of the (Z)-butylidenephthalide isomer, a pharmaceutically acceptable ester of the (Z)-butylidenephthalide isomer, or a combination thereof:

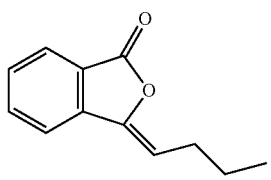

(I)

and (2) an effective amount of temozolomide, wherein (1) and (2) together provide a combination index less than 1.

2. The method as claimed in claim 1, wherein the (Z)-butylidenephthalide isomer of formula (I) is in the form of the (Z)-butylidenephthalide isomer.

3. The method as claimed in claim 1, wherein the glioma is human malignant glioma.

4. The method as claimed in claim 1, wherein the (Z)-butylidenephthalide isomer of formula (I) is administrated in form of a wafer at a daily dosage of about 30 mg/kg-body weight to about 500 mg/kg-body weight, and temozolomide is administered as a wafer at a daily dosage of about 10 mg/kg-body weight to about 100 mg/kg-body weight.

5. The method as claimed in claim 4, wherein the (Z)-butylidenephthalide isomer of formula (I) is administered at a daily dosage of about 40 mg/kg-body weight to about 120 mg/kg-body weight, and temozolomide is administrated at a daily dosage of about 40 mg/kg-body weight to about 80 mg/kg-body weight.

6. The method as claimed in claim 1, wherein the (Z)-butylidenephthalide isomer of formula (I) and temozolomide are administered together, separately, or successively.

7. The method as claimed in claim 1, wherein the (Z)-butylidenephthalide isomer of formula (I) is administered orally or administered by subcutaneous or intravenous injection and temozolomide is administered orally.

* * * * *